United States Patent [19]

Baldwin

[11] 4,119,721

[45] Oct. 10, 1978

[54] SUBSTITUTED (3-LOWERALKYLAMINO-2-$R_1$O-PROPOXY)PYRIDINES, THEIR PREPARATION AND USE

[75] Inventor: John J. Baldwin, Lansdale, Pa.

[73] Assignee: Merck & Co., Inc., Rahway, N.J.

[21] Appl. No.: 774,850

[22] Filed: Mar. 7, 1977

Related U.S. Application Data

[62] Division of Ser. No. 696,236, Jun. 15, 1976, Pat. No. 4,053,605.

[51] Int. Cl.$^2$ .................... A61K 31/44; C07D 213/57
[52] U.S. Cl. .................................. 424/263; 260/294.9
[58] Field of Search .................. 260/294.9; 424/263

[56] References Cited

U.S. PATENT DOCUMENTS

| 4,000,282 | 12/1976 | Baldwin | 260/294.9 |
| 4,001,327 | 1/1977 | Lucchesi | 260/567.6 M |
| 4,060,601 | 11/1971 | Baldwin | 424/263 |

Primary Examiner—Alan L. Rotman
Attorney, Agent, or Firm—Daniel T. Szura; Harry E. Westlake, Jr.

[57] ABSTRACT

Novel cyano substituted (3-loweralkylamino-2-acyl-O-propoxy)pyridines, their pharmaceutically acceptable salts and their preparation are disclosed. The pyridines are vasodilators having antihypertensive activity of rapid onset and extended duration and reduced tendency to cause undesirable tachychardia; they are also β-adrenergic blocking agents.

3 Claims, No Drawings

SUBSTITUTED (3-LOWERALKYLAMINO-2-R₁O-PROPOXY)PYRIDINES, THEIR PREPARATION AND USE

This is a division of application Ser. No. 696,236 filed June 15, 1976, now U.S. Pat. No. 4,053,605.

BACKGROUND OF THE INVENTION

The present invention concerns cyano substituted 2-(3-loweralkylamino-2-acyl-O-propoxy)pyridines which have antihypertensive activity of rapid onset and extended duration and are β-adrenergic blocking agents.

Hypertension in man and other animals can be treated with various chemical agents. One such class of agents is that known as the β-adrenergic blocking agents or β-blockers. While this class of agents can have antihypertensive activity, the onset of this activity is generally gradual. The structure and activity of β-blockers is generally discussed in "Clinical Pharmacology and Therapeutics" 10, 252, 306 (1969). Substituted carbocyclic aryl β-adrenergic blocking agents are disclosed in British Pat. No. 1,206,420, British Pat. No. 1,304,303, U.S. Pat. No. 3,644,636, U.S. Pat. No. 3,459,782, Belgian Pat. No. 707,050 and Netherlands Pat. No. 69.0700. Substituted N-heteroaryl β-adrenergic blocking agents are also disclosed in German application No. 2,406,930, its counterpart South African Pat. No. 74 28204, British Pat. No. 1,305,644, Journal of Medicinal Chemistry 16, 1113-1114 (1973) and Journal of Medicinal Chemistry 15, 1321 (1972).

Another class of anti-hypertensive agents are the vasodilators. Vasodilators, however, normally cause undesirable tachychardia.

Novel cyano substituted (3-loweralkylamino-2-acyl-O-propoxy)pyridines have been discovered. These compounds have antihypertensive activity of rapid onset and extended duration and they are β-adrenergic blocking agents.

SUMMARY OF THE INVENTION

Novel cyano substituted (3-loweralkylamino-2-acyl-O-propoxy)pyridines and their pharmaceutically acceptable salts which have rapid and lasting antihypertensive effect and are also β-adrenergic blocking agents.

DESCRIPTION OF THE PREFERRED EMBODIMENTS

An embodiment of the present invention is compounds selected from those having the formula

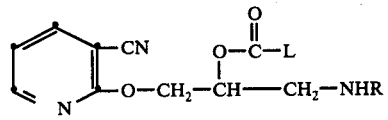   I wherein
R is $C_3$–$C_4$ branched alkyl and
L is selected from $C_1$–$C_{10}$ alkyl, phenyl, mono-and disubstituted phenyl wherein said substituents are independently selected from the gorup consisting of $C_1$–$C_4$ alkyl, $C_1$–$C_4$ alkoxy and halo,
and pharmaceutically acceptable salts thereof.

The L group includes linear and branched alkyl subh as methyl, n-decyl, tert. butyl, isoamyl, n-heptyl and the like with $C_1$–$C_4$ alkyl being preferred; mono and disubstituted phenyl such as 4-tert. butoxyphenyl, 2,6-dibromophenyl, 3-methylphenyl, 4-n-propylphenyl, 3,5-dimethoxyphenyl, 4-iodophenyl, 2-methyl-4-chlorophenyl, p-fluorophenyl and the like, with monosubstituted phenyl being preferred. The term halo includes Cl, Br, F and I, with Cl being preferred. R is isopropyl, sec. butyl or tert. butyl with tert. butyl being preferred.

More preferred compounds are those wherein L is —$CH_3$, —$C(CH_3)_3$ or p-methoxyphenyl, with —$C(CH_3)_3$ being preferred.

Most preferred compounds are the more preferred compounds where R is tert. butyl.

The substituted pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (*l*) and (*d*) or combinations of these symbols. The symbols (S) and (R) stand for sinister and rectus respectively and designate an absolute spatial configuration of the enantiomer. Where no isomer designation is given for a compound, the compound is the racemate.

The pyridines of the present invention can be prepared by any available process.

The pyridines of Formula I are conveniently prepared by treating the corresponding pyridine where the 2-propoxy substituent is —OH with an appropriate acylating agent such as an acyl halide, e.g. acetylchloride, pivaloylchloride, p-methoxybenzoxylchloride, benzoylchloride, an anhydride e.g. acetic anhydride and the like. The reaction is illustrated by the following equation:

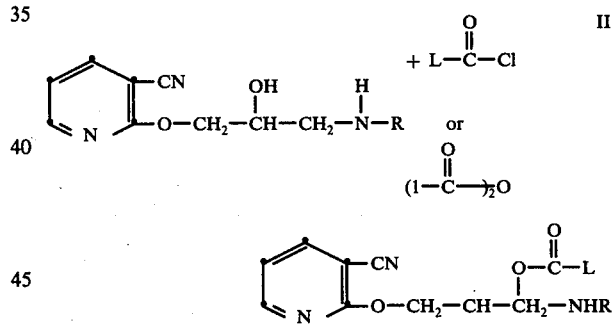

Conventional acylating conditions are employed.

The compounds of the present invention also include the pharmaceutically acceptable salts of the novel pyridines. These salts are generally salts of the pyridines and organic or inorganic acids. These salts are prepared by treating the pyridine with an appropriate amount of a useful acid, generally in a suitable solvent. Examples of useful organic acids are carboxylic acids such as maleic acid, acetic acid, tartaric acid, propionic acid, furmaric acid, isethionic acid, succinic acid, pamoic acid, oxalic acid, pivalic acid and the like; useful inorganic acids are hydrohalo acids such as HCl, HBr, HI; sulfuric acid, phosphoric acid and the like.

The compounds of the present invention have antihypertensive activity of rapid onset and are also β-adrenergic blocking agents. This antihypertensive activity is believed to be the result of peripheral vasodilation via a mechanism not directly related to β-adrenergic blockade. One advantage the present pyridines have over ordinary β-adrenergic agents is that the antihypertensive effect is immediate and generally of extended duration.

This rapid onset, antihypertensive acticity is determined by administering a representative pyridine of the present invention to spontaneously hypertensive (SH) rats and measuring the effect on blood pressure. An example of a representative compound having this antihypertensive activity is S -2-(3-tert. butylamino-2-pivaloyloxypropoxy)-3-cyanopyridine.

The β-adrenergic blocking activity of the present pyridines is determined by measuring the ability of a representative pyridine to block isoproterenol induced β-adrenergic stimulant effects such as heart rate increase, hypotension and bronchodilatation, in animals.

The ability of the present pyridines to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as antihypertensives and/or β-adrenergic blocking agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like — or dissolved, dispersed or emulsified in a suitable liquid carrier — or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form required. Conventional procedures are used to prepare the pharmaceutical formulations.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.25 mg/kg being a more preferred range. Oral administration is preferred. Either single or multiple daily doses may be administered depending on unit dosage.

Thus, another embodiment of this invention is a pharmaceutical composition containing an antihypertensive and/or β-adrenergic blocking amount of a compound of the present invention.

The following examples illustrate the preparation of representative pyridines of the present invention. Where no isomer designation is indicated, the product is the racemate. All parts are by weight unless otherwise noted. The 2-(3-tert. butylamino-2-hydroxypropoxy)-3-cyanopyridine of Example 1 is an intermediate used in Example 2.

EXAMPLE 1

S -2-(3-tert. butylamino-2-hydroxypropoxy)-3-cyanopyridine hydrochloride

To S -2-phenyl-3-tert. butyl-5-hydroxymethyloxazolidine (7 grams, 0.03 moles) in 35 ml. of N,N-dimethylformamide (DMF) is added 1.3 grams (0.03 moles of sodium hydride (57% dispersion in mineral oil). This mixture is heated 5 minutes over steam and then is allowed to stir 15 minutes at room temperature. 4.1 grams (0.03 moles) of 2-chloro-3-cyanopyridine in 20 ml of DMF is then added and the resultant reaction mixture is stirred 4 hours at room temperature. Water is then added and an oil separates. This oil is extracted three times with 25 ml of chloroform each time. This chloroform exrract is dried over sodium sulfate and concentrated under reduced pressure (20 mm) over steam to yield the product, S -2-phenyl-3-tert. butyl-5-(3-cyano-2-pyridyloxymethyl)oxazolidine, as an oil. This oil is then suspended in 1N HCl (50 ml), heated 5 minutes over steam and then is stirred for 15 minutes at room temperature. The solution obtained is then extracted twice with 25 ml of diethylether each time. The extracted aqueous layer is made basic by addition of saturated aqueous sodium carbonate solution. This aqueous solution is then extracted with ethyl acetate (3 × 25 ml) and the ethylacetate solution is dried over sodium sulfate. The dried ethyl acetate solution is then concentrated under reduced pressure (20 mm) over steam to yield an oil. This oil is chromatographed on alumina. The chromatographic fractions are concentrated to yield an oil which is dissolved in diethyl ether. Ethanolic HCl (saturated solution) is added to this ether solution until solid separation is substantially complete. The separated semi-solid is recrystallized from isopropanol/ether (ether added to isopropanol to the point of turbidity) to yield 1 gram of S -2-(3-tert. butylamino-2-hydroxypropoxy)-3-cyanopyridine hydrochloride, melting at 161°–163° C.

While in Example 1 the S-isomer of the pyridine salt is prepared, the racemate is prepared by using racemic (R,S) oxazolidine reactant; the R-isomer is prepared by using R-oxazolidine reactant.

The free amine is obtained from the Example 1 salt by any conventional procedure e.g. by treating the salt with a base (e.g. NaOH) in solution and extracting the free amine therefrom.

EXAMPLE 2

2-(3-tert. Butylamino-2-acetoxypropoxy)-3-cyanopyridine

To 2-(3-tert. butylamino-2-hydroxypropoxy)-3-cyanopyridine (1.4 g., 0.005 moles) in pyridine (10 ml) is added dropwise with stirring at 0°–5° C. acetyl chloride (0.39 g., 0.005 moles). The solution is stirred 15 min. at 0°–5° C. then 18 hr. at room temperature. The mixture is concentrated under reduced pressure (25 mm); the resulting residue is extracted with chloroform and saturated aqueous sodium carbonate solution. The organic layer is separated, dried over $Na_2SO_4$ and concentrated under reduced pressure (25 mm). The residue is dissolved in acetonitrile (5 ml) and a solution of maleic acid (0.005 moles) in acetonitrile is added. 2-(3-tert. Butylamino-2-acetoxypropoxy)-3-cyanopyridine separates, is filtered and recrystallized from acetonitrile yielding 350 mg of maleate salt melting at 153°–155° C.

Using trimethylacetylchloride in place of acetyl chloride - yields 2-(3-tert. butylamino-2-pivaloyloxypropoxy)-3-cyanopyridine which is purified as the hydrochloride salt, melting at 217°–218° C.

Using p-methoxybenzoylchloride in place of actyl chloride yields 2-[3-tert. butylamino-2-(4-methoxybenzoyloxy)-propoxy]-3-cyanopyridine which is purified as the hydrogen maleate salt, melting at 175°–176° C.

Isopropyl or sec. butyl amino analogues of the compounds of the above examples are prepared by substituting suitable oxazolidines e.g. 2-phenyl-3-isopropyl-5-hydroxymethyloxazolidine, (S)-2-methyl-3-sec. butyl-5-hydroxymethyloxazolidine, 3-isopropyl-5-hydroxymethyloxazolidine for the (S)-2-phenyl-3-tert. butyl-5-hydroxymethyloxazolidine reactant.

The present invention also includes the quaternary ammonium salts and N-pyridine oxides of the Formula I compounds.

The quaternary ammonium salts have the formula:

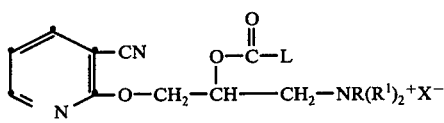
III wherein R and L are defined as above, $R^1$ is an alkyl (e.g. $C_1-C_4$ alkyl) or aryl (e.g. benzyl) group and X is a halogen especially Cl, Br or I. These quaternary salts are prepared using any convenient method. For example, they can be prepared by treating the compound of Formula I with an alkyl or aryl halide such as methyl iodide or benzyl chloride to obtain the corresponding quaternary salt of Formula III.

The N-pyridine oxides have the formula:

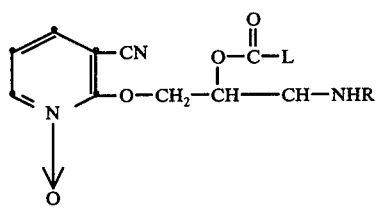
IV wherein R and L are defined as above, including the acid addition salts and quaternary ammonium salts thereof. These N-oxides are also prepared using conventional reagents and procedure. For example, a convenient method of preparing these oxides is to treat the intermediate 2-chloro-3-cyanopyridine with an oxidizing agent e.g. $H_2O_2$ using conventional reaction conditions to produce the oxidized intermediate having the formula:

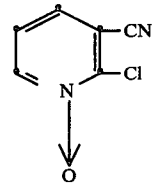
V

The formula V compound is then substituted for the 2-chloro-3-cyanopyridine in Example 1 to obtain the N-pyridine oxide having the formula:

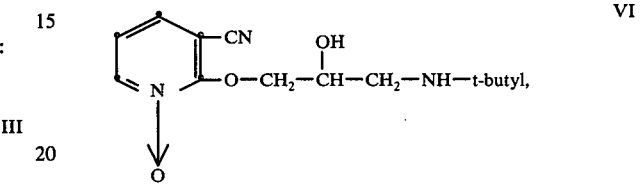
VI which in turn is acylated to produce the corresponding N-oxide having the formula:

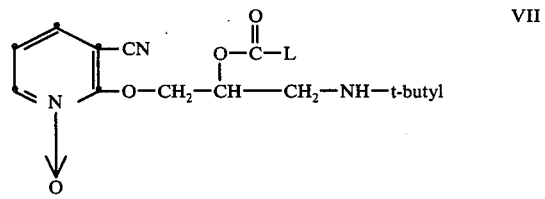
VII

Claims to the invention follow.
What is claimed is:
1. A compound having the formula:

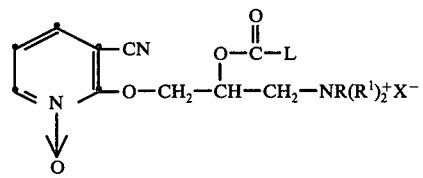

wherein
R is $C_3-C_4$ branched alkyl,
$R^1$ is $C_1-C_4$ alkyl or benzyl
L is selected from $C_1-C_{10}$ alkyl, phenyl, mono- and disubstituted phenyl wherein said substituents are independently selected from $C_1-C_4$ alkyl, $C_1-C_4$ alkoxy and halo, and
X is halogen.
2. A pharmaceutical composition containing an antihypertensive effective amount of a compound of claim 1 and pharmaceutical compounding ingredient.
3. A method of treating hypertension in animals which comprises administering an effective amount of a compound of claim 1.

* * * * *